(12) United States Patent
Shin et al.

(10) Patent No.: US 8,053,093 B2
(45) Date of Patent: Nov. 8, 2011

(54) ORGANOMETALLIC COMPLEX, METHOD OF PREPARING THE SAME AND ORGANIC LIGHT EMITTING DEVICE COMPRISING THE SAME

(75) Inventors: Jung-Han Shin, Suwon-si (KR); Seung-Gak Yang, Suwon-si (KR); Hee-Yeon Kim, Suwon-si (KR); Chang-Ho Lee, Suwon-si (KR); Hee-Joo Ko, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 601 days.

(21) Appl. No.: 12/155,940

(22) Filed: Jun. 11, 2008

(65) Prior Publication Data

US 2008/0311427 A1   Dec. 18, 2008

(30) Foreign Application Priority Data

Jun. 13, 2007   (KR) .................. 10-2007-0058006

(51) Int. Cl.
*H01J 1/63* (2006.01)
(52) U.S. Cl. .................. 428/690; 546/7; 313/504
(58) Field of Classification Search .................. 428/690; 313/504; 546/7
See application file for complete search history.

(56) References Cited

U.S. PATENT DOCUMENTS 5,858,563 A * 1/1999 Sano et al. .................. 428/690
6,362,339 B1   3/2002 McCormick

FOREIGN PATENT DOCUMENTS

JP   11-040355 * 2/1999

OTHER PUBLICATIONS

Tommasi et. al., Synthesis of Pyrroloquinolinequinone Analogs..., 1995, Inorganic Chemistry, vol. 34, pp. 1514-1523.*

Korean Office Action issued by Korean Patent Office on Apr. 9, 2009 corresponding Korean Patent Application No. 10-2007-0058006 and Request for Entry of the Accompanying Office Action attached herewith.

* cited by examiner

*Primary Examiner* — Jennifer Chriss
*Assistant Examiner* — Gregory Clark
(74) *Attorney, Agent, or Firm* — Robert E. Bushnell, Esq.

(57) ABSTRACT

An organometallic complex for an organic light emitting device represented by formula 1, a method of preparing the same and an organic light emitting device including the same:

(1)

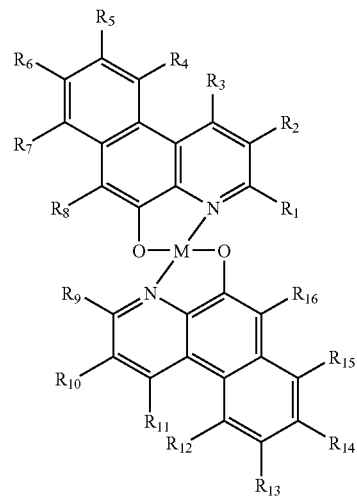

where $R_1$ through $R_{16}$ are a hydrogen atom, a cyano group, a hydroxyl group, a nitro group, a halogen atom, a $C_1$-$C_{20}$ alkyl group, a $C_1$-$C_{20}$ alkoxy group, a $C_6$-$C_{20}$ aryl group, a $C_7$-$C_{20}$ arylalkyl group, a $C_2$-$C_{20}$ alkylalkoxy group, a $C_7$-$C_{20}$ arylalkoxy group, a $C_6$-$C_{20}$ arylamino group, a $C_1$-$C_{20}$ alkylamino group, a $C_6$-$C_{20}$ heteroarylamino group, and a $C_2$-$C_{20}$ heteroring group; and M is a bivalent metal such as Be, Mg, Zn, Ca, Cr, Fe, Co, Ni and Cu. The compound represented by Formula 1 can be effectively used in an electron transport layer or an electron injection layer. An organic light emitting device including the compound represented by Formula 1 can thus have long lifetime.

19 Claims, 2 Drawing Sheets

| SECOND ELECTRODE |
|---|
| ELECTRON INJECTION LAYER (EIL) |
| ELECTRON TRANSPORT LAYER (ETL) |
| EMITTING LAYER (EML) |
| HOLE TRANSPORT LAYER (HTL) |
| HOLE INJECTION LAYER (HIL) |
| FIRST ELECTRODE |
| SUBSTRATE |

ORGANOMETALLIC COMPLEX, METHOD OF PREPARING THE SAME AND ORGANIC LIGHT EMITTING DEVICE COMPRISING THE SAME

CROSS-REFERENCE TO RELATED PATENT APPLICATION AND CLAIM OF PRIORITY

This application claims the benefit of Korean Patent Application No. 10-2007-0058006, filed on Jun. 13, 2007, in the Korean Intellectual Property Office, the disclosure of which is incorporated herein in its entirety by reference.

BACKGROUND OF THE INVENTION

1. Field of the Invention

The present invention relates to an organometallic complex and an organic light emitting device including the same.

2. Description of the Related Art

Electroluminescent emitting devices, which are self-emitting devices, have the advantages of having wide viewing angles, excellent contrast, and quick response, and thus have drawn a large amount of public attention. The electroluminescent emitting device is classified into two types, an inorganic light emitting device which includes an inorganic compound in an emitting layer and an organic light emitting device (OLED) which includes an organic compound in an emitting layer. The OLED has higher brightness, a lower operating voltage, a quicker response, and can realize more colors compared to the inorganic light emitting device, and thus much research thereon has been carried out.

Typically, an OLED has an anode/organic emitting layer/cathode structure. An OLED can also have various other structures, such as an anode/organic emitting layer/hole blocking layer/cathode structure, an anode/organic emitting layer/electron transport layer/cathode structure, or an anode/organic emitting layer/hole blocking layer/electron injection layer/cathode structure by interposing a hole blocking layer, an electron transport layer, and/or an electron injection layer between the emitting layer and the cathode.

A metal complex such as aluminum(III) tris(8-hydroxyquinolate) (Alq3), or bis(10-hydroxybenzo[h]quinolinato) beryllium (BeBq2) can be used as an electron transport material. Although Alq3 has excellent stability, properties thereof need to be improved. In contrast, although BeBq2 has excellent electron transport capability because of high stacking of aromatic rings among molecules, stability thereof is not sufficient. Thus, lifetime, efficiency and power input characteristics of those materials do not meet desired levels. Accordingly, there is a need for improving those characteristics.

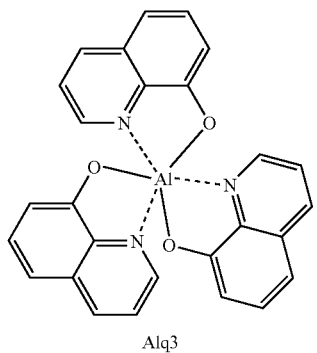

Alq3

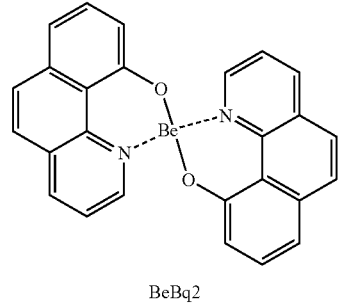

BeBq2

SUMMARY OF THE INVENTION

The present invention provides an improved organometallic complex.

According to an aspect of the present invention, there is provided an organometallic complex for an organic light emitting device represented by Formula 1 below.

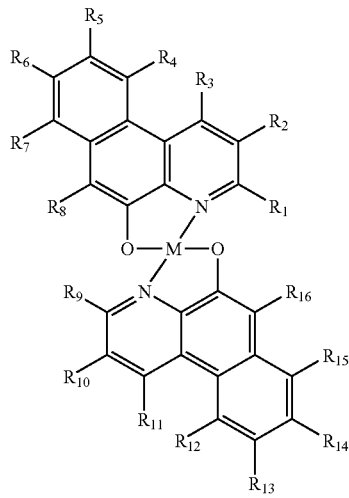

Formula 1

Here, $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group; and M is a bivalent metal selected from the group consisting of Be, Mg, Zn, Ca, Cr, Fe, Co, Ni and Cu.

According to another aspect of the present invention, there is provided a method of preparing an organometallic complex represented by Formula 1, the method includes reacting benzoquinolinol derivatives (A) and (A') and a bivalent metal complex (B).

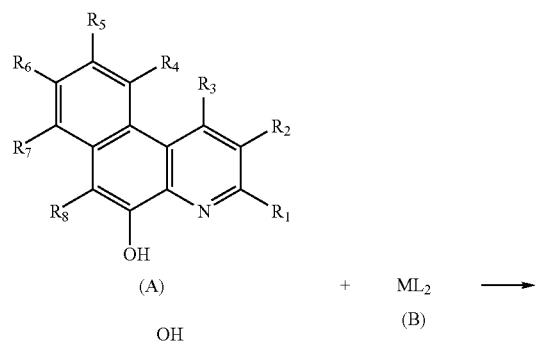

(A)      +   ML₂   →
              (B)

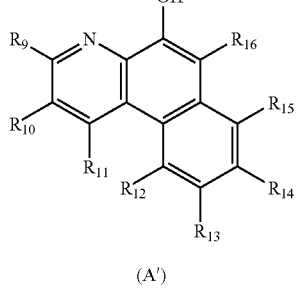

(A')

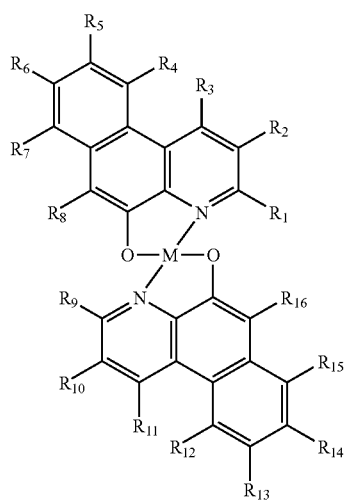

Formula 1

Here, $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group, and M is a bivalent metal selected from the group consisting of Be, Mg, Zn, Ca, Cr, Fe, Co, Ni and Cu, and L is a monovalent anion ligand.

According to another aspect of the present invention, there is provided an organic light emitting device comprising a single organic layer or multi organic layers between a first electrode and a second electrode, wherein the organic layer comprises an organometallic complex represented by Formula 1 above.

The organometallic complex has high stability and excellent electron transport capability, and thus effectively used as a material that is used to form an organic layer. Therefore, an organic light emitting device having low operating voltage and long lifetime can be obtained.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
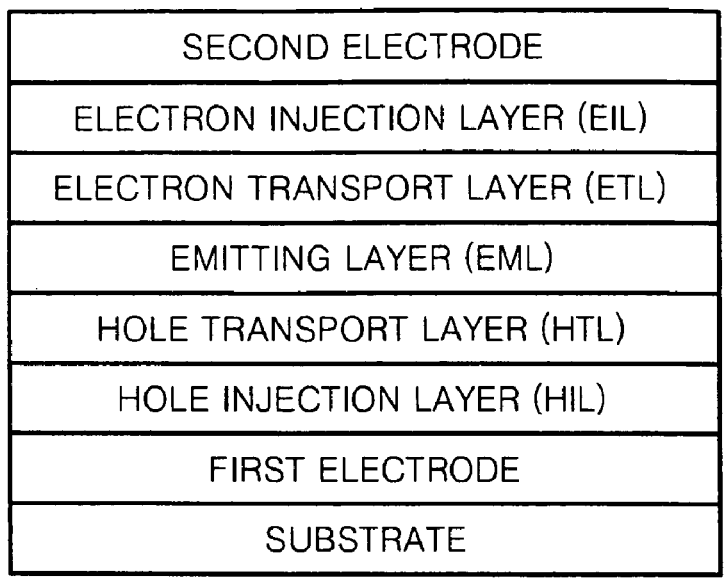
FIGS. 1A and 1B schematically show structures of examples of organic light emitting devices.

Hereinafter, the present invention will now be described more fully with reference to the accompanying drawings, in which exemplary embodiments of the invention are shown.

An organometallic complex for an organic light emitting device according to an embodiment of the present invention is a complex formed by a bivalent metal and two benzoquinolinol derivative ligands.

The organometallic complex is represented by Formula 1 below.

Formula 1

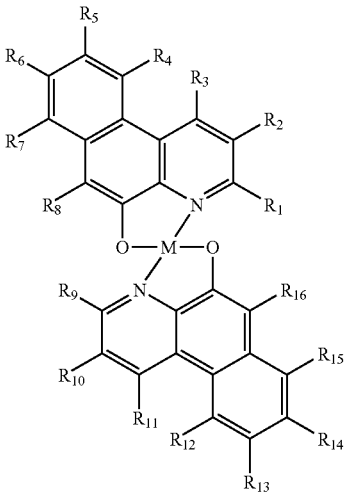

Here, $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group; and M is a bivalent metal selected from the group consisting of Be, Mg, Zn, Ca, Cr, Fe, Co, Ni and Cu, and is preferably Zn, Be, or Mg.

Examples of the unsubstituted $C_1$-$C_{20}$ alkyl group may include methyl, ethyl, propyl, isobutyl, sec-butyl, pentyl, iso-amyl, and hexyl. Examples of the unsubstituted $C_1$-$C_{20}$ alkyl group may include the $C_1$-$C_{20}$ alkyl group, wherein at least one hydrogen atom in the unsubstituted $C_1$-$C_{20}$ alkyl group may by substituted with a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkenyl group, a $C_1$-$C_{20}$ alkynyl group, a $C_6$-$C_{20}$ aryl group, a $C_7$-$C_{20}$ arylalkyl group, a $C_2$-$C_{20}$ heteroaryl group, or a $C_3$-$C_{20}$ heteroarylalkyl group.

Examples of the unsubstituted $C_1$-$C_{20}$ alkoxy group may include methoxy, ethoxy, phenyloxy, cyclohexyloxy, naphthyloxy, isopropyloxy, and diphenyloxy. Examples of the unsubstituted $C_1$-$C_{20}$ alkoxy group may include the $C_1$-$C_{20}$ alkoxy group wherein at least one hydrogen atom in the unsubstituted $C_1$-$C_{20}$ alkoxy group may be substituted with the same substituent described above for the $C_1$-$C_{20}$ alkyl group.

The unsubstituted $C_6$-$C_{20}$ aryl group refers to a carbocyclic aromatic hydrocarbon group having 6-20 carbon atoms, and the $C_6$-$C_{20}$ aryl group may include a single ring or rings fused or attached to each other using a pendent manner. Examples of the $C_6$-$C_{20}$ aryl group may include phenyl, naphthyl, and tetrahydronaphthyl. At least one hydrogen atom in the $C_6$-$C_{20}$ aryl group may be substituted with the same substituent described above for the $C_1$-$C_{20}$ alkyl group.

The unsubstituted $C_7$-$C_{20}$ arylalkyl group used herein refers to an aryl group, wherein at least one hydrogen atom of the aryl group is substituted with a substituent, for example, a short chain alkyl radical such as a methyl group, an ethyl group, and a propyl group. Examples of the $C_7$-$C_{20}$ arylalkyl group may include a benzyl group, and a phenylethyl group. At least one hydrogen atom in the $C_7$-$C_{20}$ arylalkyl group may be substituted with the same substituent described above for the $C_1$-$C_{20}$ alkyl group.

The functional groups other than described above are interpreted as commonly accepted in the art.

According to an embodiment of the present invention, the organometallic complex for an organic light emitting device may be represented by Formulae 2 through 7 below. However, the present invention is not limited thereto.

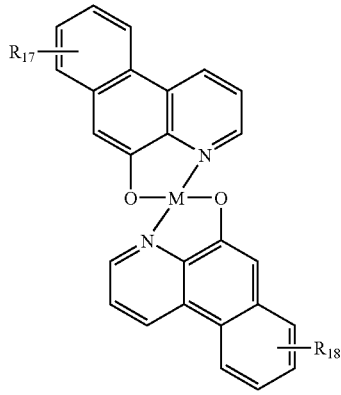

Formula 2

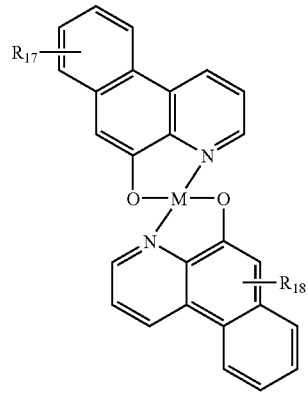

Formula 3

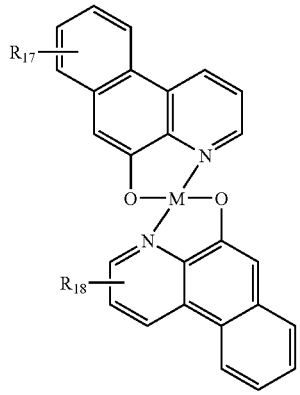

Formula 4

Formula 5

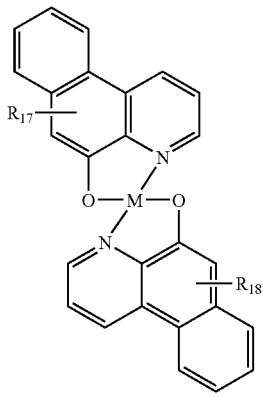

Formula 6

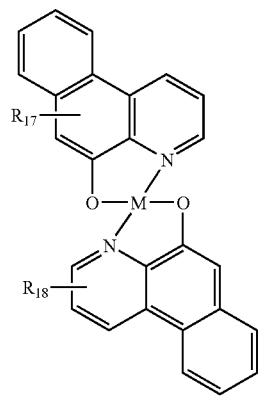

Formula 7

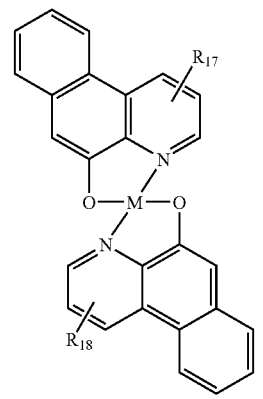

The organometallic complex represented by Formula 1 may be represented by one selected from the group consisting of Formulae 8 through 10 below.

Formula 8

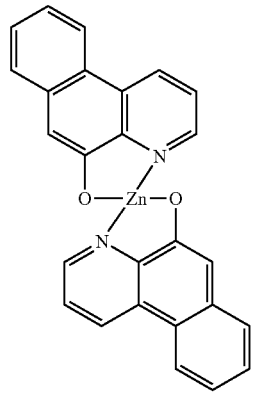

Formula 9

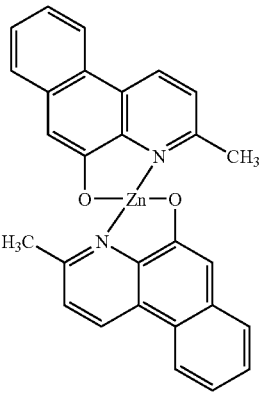

Formula 10

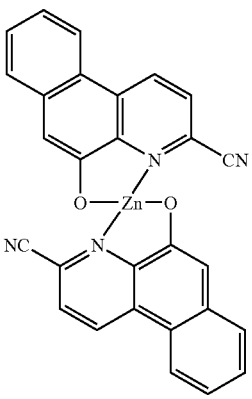

Here, M is a bivalent metal selected from the group consisting of Be, Mg, Zn, Ca, Cr, Fe, Co, Ni and Cu, and $R_{17}$ and $R_{18}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group.

The organometallic complex for an organic light emitting device according to an embodiment of the present invention has excellent electron transport capability since stacking among molecules increases using benzoquinolinol derivatives as ligands, and has high stability since a ligand and a core metal forms a stable coordinate bond. The organometallic complex can be used as a material that is used to form an electron transport layer and an electron injection layer as well as an emitting layer. When the organometallic complex is used in a light emitting device, an organic light emitting device having long lifetime and high efficiency can be obtained.

The organometallic complex represented by Formula 1 can be prepared though Reaction Scheme 1 below.

Reaction Scheme 1

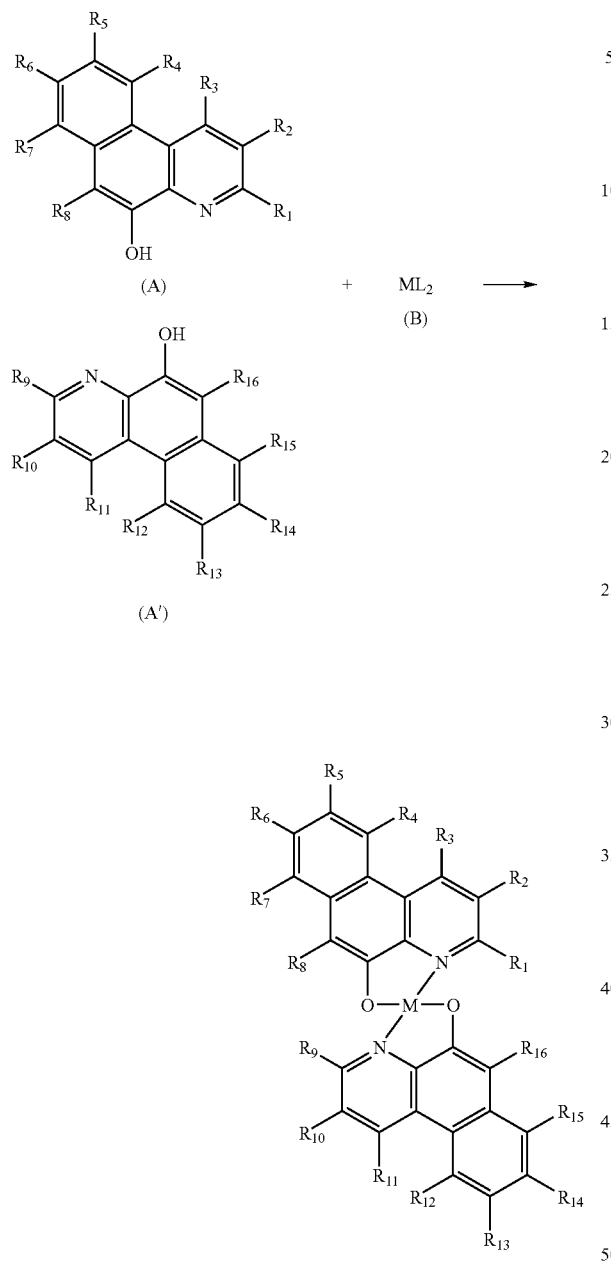

Formula 1

Reaction Scheme 2

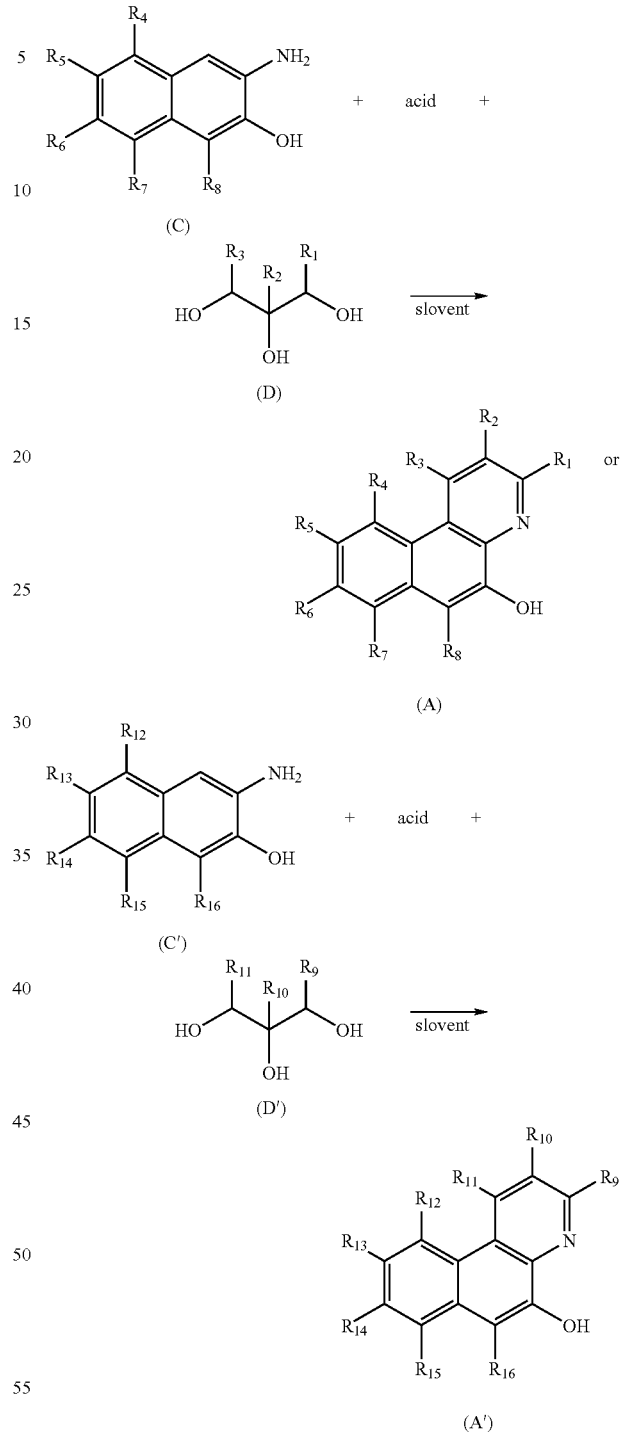

Here, (A) and (A') may be the same or different benzoquinolinol derivatives, and (B) may be a hydrated form of a bivalent metal complex.

L in the compound (B) is a monovalent anion ligand.

$R_1$ to $R_{16}$ in Reaction Scheme 1 are as described above with respect to Formula 1.

Meanwhile, the benzoquinolinol derivative (A) or (A') may be prepared through Reaction Scheme 2 below.

In Reaction Scheme 2, the reaction between the naphthalene derivative (C) and the glycerol derivative (D) or the reaction between the naphthalene derivative (C') and the glycerol derivative (D') may be carried out in the presence of an acid, and the solvent is not limited.

In Reaction Scheme 2, $R_1$ to $R_{16}$ are as described above with respect to Formula 1.

Particularly, L of the bivalent metal complex (B) may be R'COO⁻, where R' may be a $C_1$-$C_5$ alkyl group, such as methyl, ethyl, n-propyl, iso-propyl, n-butyl, sec-butyl, iso-butyl, n-pentyl, sec-pentyl, iso-pentyl or neo-pentyl. More particularly, L of the bivalent metal complex is an acetyl group.

The reaction in Reaction Scheme 1 may be carried out in the presence of a $C_1$-$C_{20}$ alcohol solvent. Examples of the $C_1$-$C_{20}$ alcohol solvent may include methanol, ethanol, or iso-propanol, but are not limited thereto.

An organic light emitting device according to an embodiment of the present invention may further include a single organic layer or multi organic layers between a first electrode and a second electrode, wherein the organic layer may include an organometallic complex represented by Formula 1.

The organic light emitting device may have various structures. The organic light emitting device may include at least one layer selected from the group consisting of a hole injection layer, a hole transport layer, an emitting layer, a hole blocking layer, an electron transport layer and an electron injection layer as an organic layer between the first electrode and the second electrode. These organic layers may include the organometallic complex represented by Formula 1. For example, an organic layer including the organometallic complex represented by Formula 1 in the organic light emitting device may be an electron transport layer or an electron injection layer, but is not limited thereto.

Figure 1B:
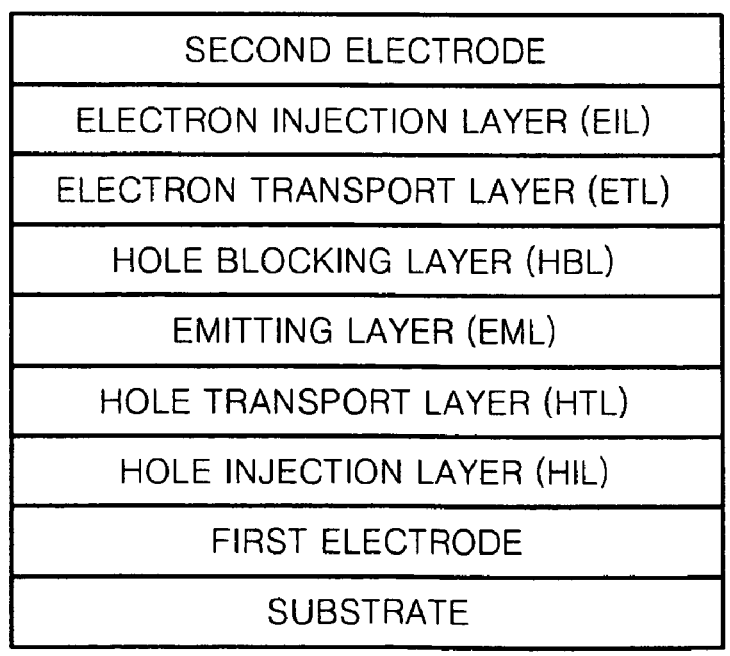

More particularly, structures of the organic light emitting device according to an embodiment of the present invention are shown in FIGS. 1A and 1B.

The organic light emitting device shown in FIG. 1A has a first electrode/hole injection layer/hole transport layer/emitting layer/electron transport layer/electron injection layer/second electrode structure. The organic light emitting device shown in FIG. 1B has a first electrode/hole injection layer/hole transport layer/emitting layer/hole blocking layer/electron transport layer/electron injection layer/second electrode structure. Here, the electron transport layer or the electron injection layer may include the organometallic complex represented by Formula 1.

A method of preparing the organic light emitting device having structures described above will be described.

First, an anode as a first electrode is formed on a substrate by depositing or sputtering a high work-function material that is used to form an anode. The substrate, which can be any substrate that is used in conventional organic electroluminescent devices, may be a glass substrate or a transparent plastic substrate that has excellent transparency, and surface smoothness, is easily treated, and is waterproof. ITO, IZO, $SnO_2$, ZnO, and any transparent material which has high conductivity may be used as the material that is used to form the anode.

A hole injection material is formed on the anode using thermal vacuum deposition or spin coating. Examples of the material that can be used to form the hole injection layer may include a phthalocyanine compound such as CuPc or copper-phthalocyanine disclosed in U.S. Pat. No. 4,356,429 which is incorporated herein by reference, a star-burst type amine derivative such as TCTA, m-MTDATA or m-MTDAPB disclosed in Advanced Material, 6, p. 677 (1994) which is incorporated herein by reference, a conductive polymer such as polyaniline/dodecylbenzenesulfonic acid (Pani/DBSA), poly (3,4-ethylenedioxythiophene)/poly(4-styrenesulfonate) (PEDOT/PSS), polyaniline/camphor sulfonic acid (Pani/CSA) or (polyaniline)/poly (4-styrene-sulfonate) (PANI/PSS), but are not limited thereto.

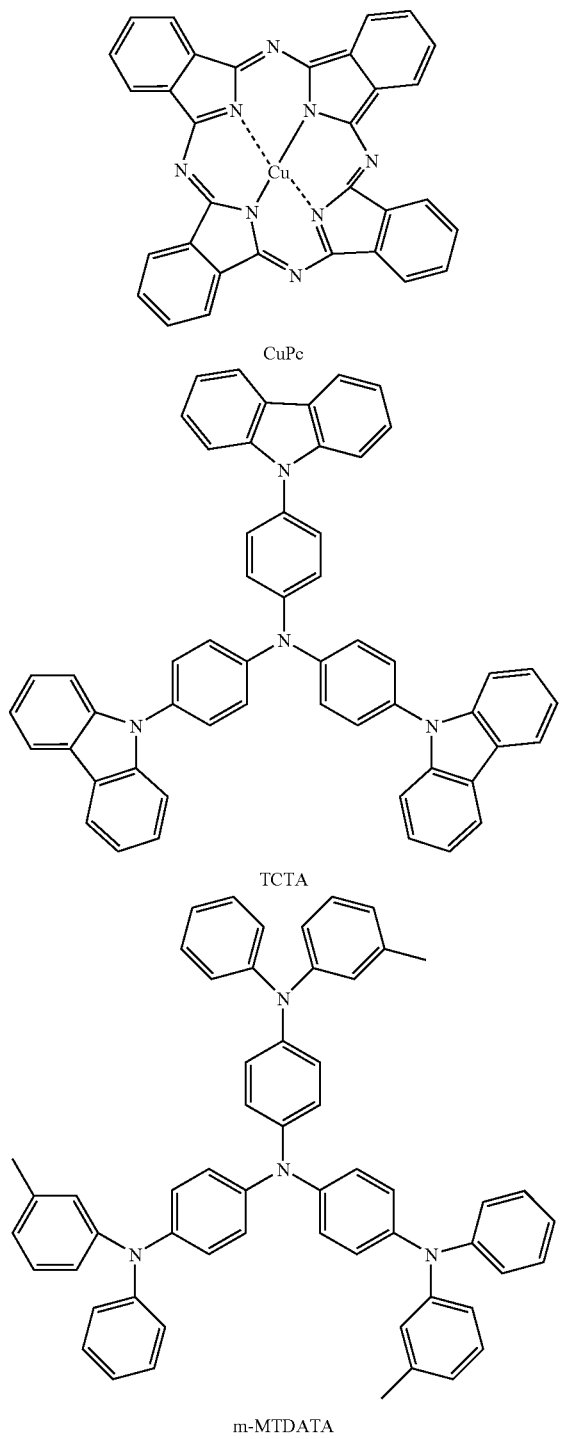

A hole transport layer is formed using thermal vacuum deposition or spin coating of a hole transport material on the hole injection layer. Examples of the material that can be used to form the hole transport layer may include, for example, 1,3,5-tricarbazolylbenzene, 4,4'-biscarbazolylbiphenyl, polyvinylcarbazole, m-biscarbazolylphenyl, 4,4'-biscarbazolyl-2,2'-dimethylbiphenyl, 4,4',4"-tri(N-carbazolyl)triphenylamine, 1,3,5-tri(2-carbazolylphenyl)benzene, 1,3,5-tris (2-carbazolyl-5-methoxyphenyl)benzene, bis(4-carbazolylphenyl)silane, N,N'-bis(3-methylphenyl)-N,N'- diphenyl-[1,1-biphenyl]-4,4'diamine (TPD), N,N'-di(naphthalene-1-il)-N,N'-diphenyl benzidine (α-NPD), N,N'-diphenyl-N,N'-bis(1-naphthyl)-(1,1'-biphenyl)-4,4'-diamine (NPB), poly(9,9-dioctylfluorene-co-N-(4-butylphenyl) diphenylamine) (TFB) and poly(9,9-dioctylfluorene-co-bis-(4-butylphenyl-bis-N,N-phenyl-1,4-phenylenediamin) (PFB), but are not limited thereto.

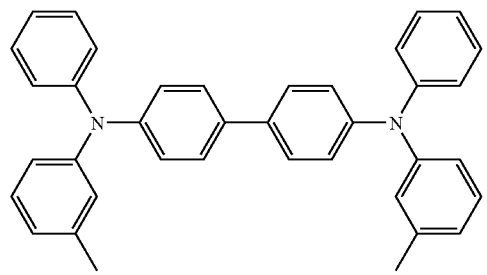

TPD

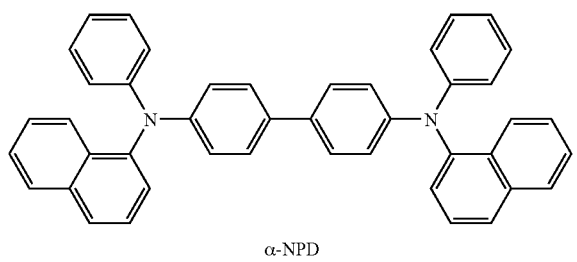

α-NPD

Then, an emitting layer is formed on the hole transport layer. The material that is used to form the emitting layer is not limited. A host material may be 4,4'-biscarbazolylbiphenyl (CBP), TCB, TCTA, SDI-BH-18, SDI-BH-19, SDI-BH-22, SDI-BH-23, dmCBP, Liq, TPBI, Balq, or BCP. As for a dopant material, a fluorescent dopant such as IDE102 or IDE105 obtained from Idemitsu Kosan Co., Ltd. and a phosphorescent dopant such as Ir(ppy)3 known as a green phosphorescent dopant, and (4,6-F2 ppy)2Irpic known as a blue phosphorescent dopant may be thermally co-deposited.

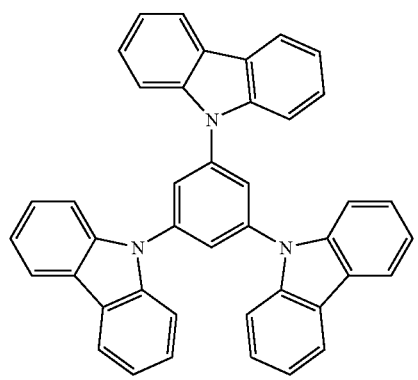

TCB

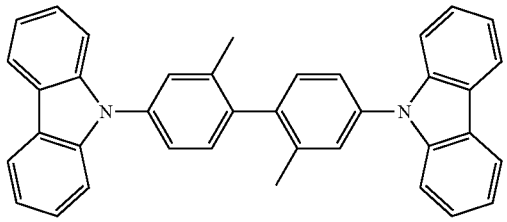

dmCBP

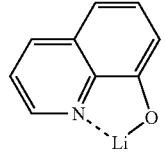

Liq

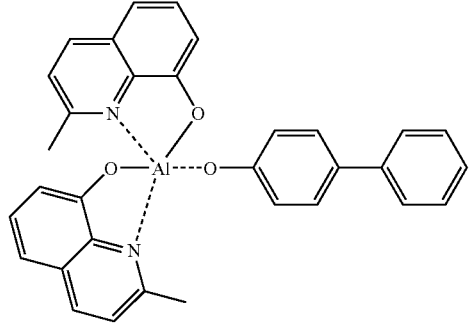

Balq

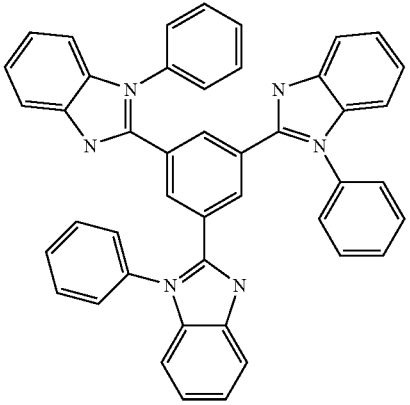

TPBI

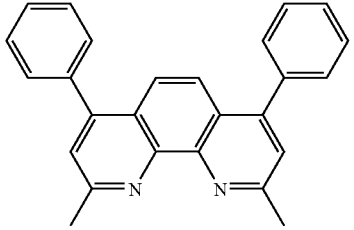

BCP

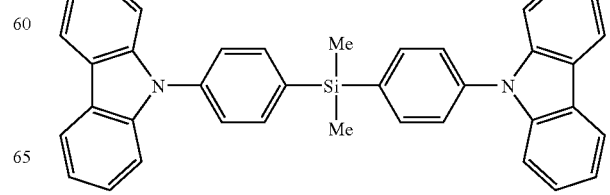

SDI-BH-18

SDI-BH-19

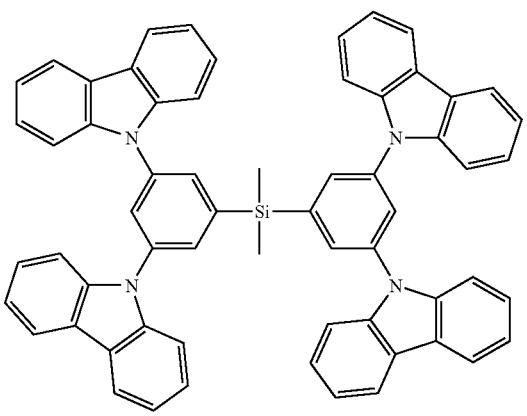

SDI-BH-22

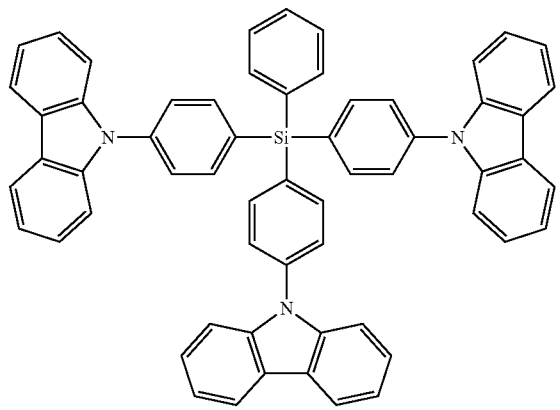

SDI-BH-23

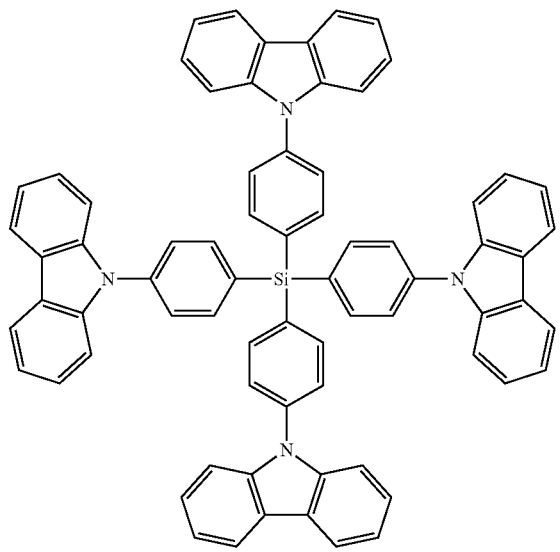

The doping concentration is, in general, 0.5 to 12 w %, but is not limited thereto.

An electron transport layer may be formed on the emitting layer using vacuum deposition or spin coating.

A hole blocking layer may further be formed using thermal vacuum deposition of a material blocking holes to prevent diffusion of triplet excitons or holes into an electron transport layer when a phosphorescent dopant is used to form the emitting layer. The material that is used to form the hole blocking layer may have electron transport capability and higher ionization potential than a light emitting compound and, and may be Balq, BCP, but is not limited thereto.

An electron transport layer may be formed on the hole blocking layer using vacuum deposition or spin coating. The organometallic complex represented by Formula 1 may be used alone or in combination with Alq3 which is known as a material that can be used to form the electron transport layer.

An electron injection layer may be formed on the electron transport layer. A material that is used to form the electron injection layer may include LiF, NaCl, CsF, $Li_2O$, or BaO, but is not limited thereto. Further, the material may include the organometallic complex represented by Formula 1.

A cathode as a second electrode is formed on the electron injection layer using thermal vacuum deposition of a metal that is used to form the cathode to prepare an organic light emitting device. The metal that is used to form the cathode may be Li, Mg, Al, Al—Li, Ca, Mg—In, Mg—Ag or the like, or ITO or IZO can be used to form a transparent cathode to obtain a single layered top emission light emitting device as desired. The organic light emitting device according to an embodiment of the present invention may be formed further with one or two intermediate layers.

The present invention will be described in more detail with reference to Synthesis Examples of an organometallic complex represented by Formula 8 (Compound 1) and Examples below, but is not limited thereto. The following examples are for illustrative purposes only and are not intended to limit the scope of the invention.

Example 1

Preparation of Organometallic Complex (1) Synthesis of benzo[f]quinolin-5-ol

Compound A (benzo[f]quinolin-5-ol) was synthesized through Reaction Scheme 3.

Reaction Scheme 3

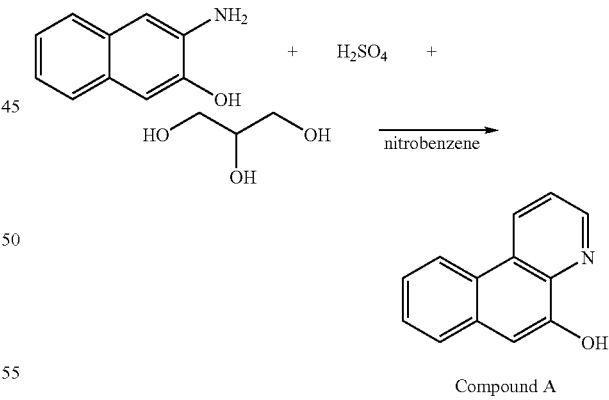

Compound A 35 g of 3-Amino-2-naphthol, 57 g of glycerol, 2 L of nitrobenzene were added to a 2 L round bottom flask, and 53 g of sulfuric acid was added thereto in an ice bath, and then the round bottom flask was gradually heated. After 9 hours of reaction, the flask was cooled down to 50° C., and the reaction solution was gradually poured in 2 L of ice water. The result solution was subjected to extraction using 8 L of ethylacetate to maximize nitrobenzene removal. $NH_4OH$ was added to neutralize the solution to pH 8, and the solution was filtered to remove tar. The remaining solution was subjected to extraction using 10 L of ethylacetate and then concentrated. The concentrated solution was separated using a column chromatography. A mixture of hexane:ethylacetate in a ratio of 20:1 was used as a developing solvent. The obtained solid was washed using 300 ml of a mixture of hexane:ethylacetate in a ratio of 50:1, and dried in a vacuum for one hour to obtain 12.1 g of benzo[f]quinolin-5-ol (Compound A) 12.1 g (Yield: 16.4%)

$^1$H NMR (300 MHz, Acetone-d6) δ 9.22 (d, 1H), 8.96 (d, 1H), 8.70 (d, 1H), 7.88 (d, 1H), 7.79 (m, 1H), 7.60 (m, 2H), 7.41 (s, 1H)

(2) Preparation of Organometallic Complex

Compound 1 was synthesized through Reaction Scheme 4 below.

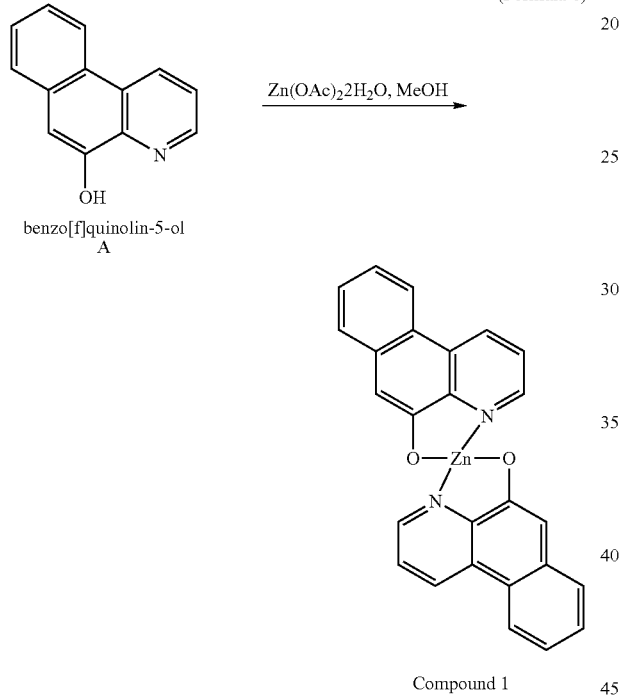

5 g (2.56×10$^{-2}$ mole) of Compound A (benzo[f]quinolin-5-ol) and 2.8 g (1.27×10$^{-2}$ mole) of zinc acetate dihydrate (Zn(OAc)$_2$2H$_2$O) were dissolved in 200 mL of MeOH and stirred at a reflux temperature for 18 hours. The obtained white solid was filtered and sequentially washed with MeOH and diethyl ether to obtain 4.3 g of Compound 1 represented by Formula 8.

$^1$H-NMR (DMSO-d$_6$ 400 MHz) δ(ppm) 9.40 (2H, d), 9.00 (2H, d), 8.61 (2H, d), 7.90-7.88 (2H, m), 7.63 (2H, d), 7.47 (2H, t), 7.28 (2H, t), 7.01 (2H, s)

Example 2

Preparation of Organic Light Emitting Device

An organic light emitting device having a structure described below was prepared using Compound 1 synthesized in Example 1 as an electron transport layer: ITO glass/ m-MTDATA(750 Å)/α-NPD(150 Å)/DSA(300 Å):TBPe (3%)/Compound 1 (200 Å)/LiF(80 Å)/Al(3000 Å)

A 15 Ω/cm$^2$ (1200 Å) ITO glass substrate (manufactured by Corning Inc.) was cut into pieces of 50 mm×50 mm×0.7 mm in size, then the pieces were ultrasonic cleaned in isopropyl alcohol and deionized water for 5 minutes for each, and then the pieces were UV ozone cleaned for 30 minutes to be used as an anode. Then, m-MTDATA was vacuum deposited to a thickness of 750 Å on the ITO substrate to form a hole injection layer. α-NPD was then vacuum deposited to a thickness of 150 Å on the hole injection layer to form a hole transport layer. After the hole transport layer was formed, an emitting layer was formed to a thickness of 300 Å by vacuum depositing distyrylanthracene (DSA) as a host and 3% of tetra(t-butyl)perylene (TBPe) as a dopant on the hole transport layer. Then, Compound 1 was vacuum deposited to a thickness of 200 Å on the emitting layer to form an electron transport layer. LiF was vacuum deposited to a thickness of 80 Å as an electron injection layer on the electron transport layer and Al was vacuum deposited to a thickness of 3000 Å as a cathode thereon to form a LiF/Al electrode to complete an organic electroluminescent device as illustrated in FIG. 1A.

Comparative Example 1

An organic light emitting device having the structure described below was prepared in the same manner as in Example 1 except that Alq3 was used as an electron transport layer: ITO glass/m-MTDATA(750 Å)/α-NPD(150 Å)/DSA (300 Å):TBPe(3%)/Alq3(200 Å)/LiF(80 Å)/Al(3000 Å).

Comparative Example 2

An organic light emitting device having the structure described below was prepared in the same manner as in Example 1 except that Znq2 was used as an electron transport layer: ITO glass/m-MTDATA(750 Å)/α-NPD(150 Å)/DSA (300 Å):TBPe(3%)/Znq2(200 Å)/LiF(80 Å)/Al(3000 Å).

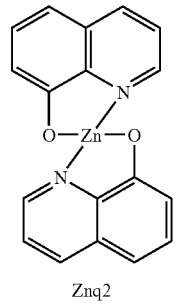

Znq2

Evaluation Example

Figure 2:
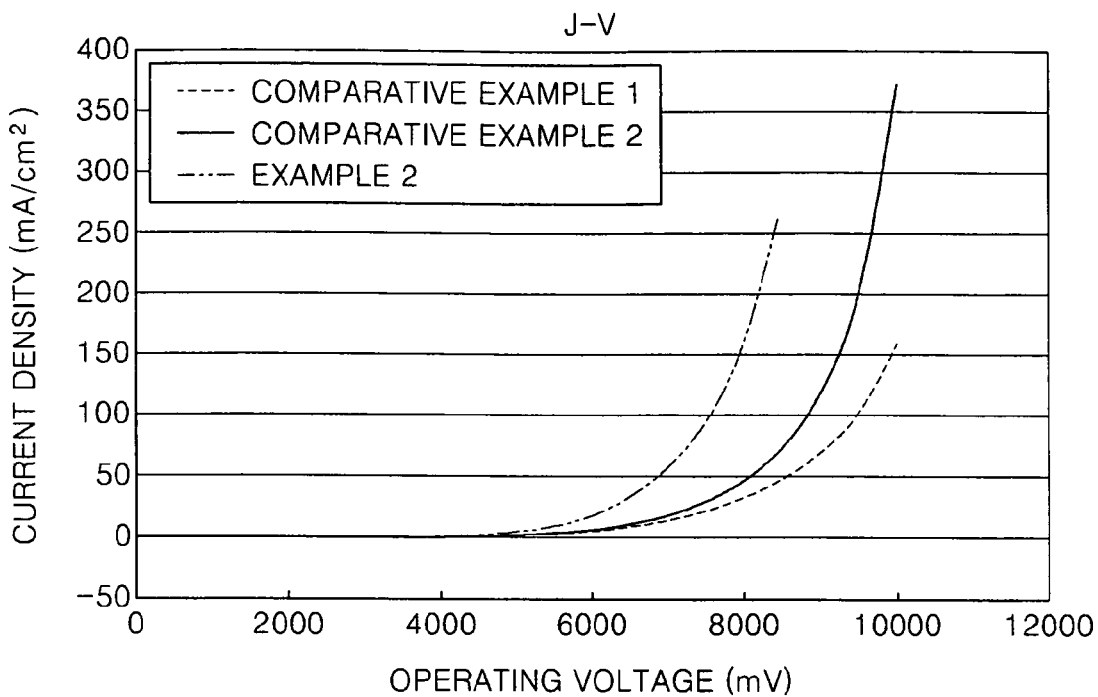
FIG. 2 shows a graph illustrating current-voltage characteristics of organic light emitting devices according to Example 2 and Comparative Examples 1 and 2.

Current-voltage characteristics of organic light emitting devices according to Example 2, Comparative Example 1 and Comparative Example 2 were evaluated and the results are shown in Table 1 below and a graph illustrating the characteristics is shown in FIG. 2. The current-voltage evaluation was performed using Keithley.

Figure 3:
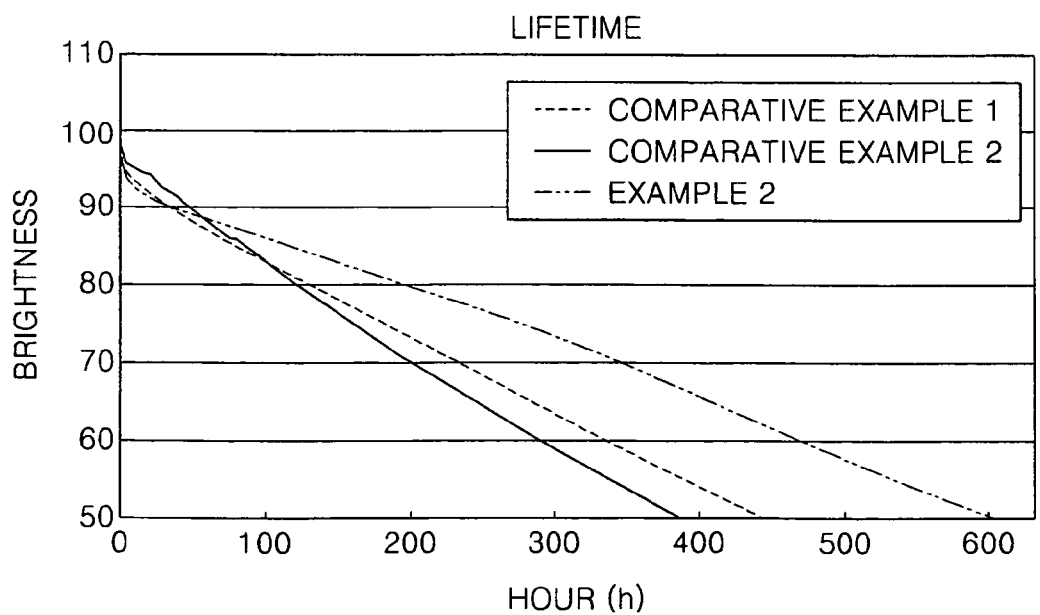
FIG. 3 shows a graph illustrating lifetime characteristics of organic light emitting devices according to Example 2 and Comparative Examples 1 and 2.

In addition, lifetime characteristics of organic light emitting devices according to Example 2, Comparative Example 1 and Comparative Example 2 were evaluated and the results are shown in Table 1 and a graph illustrating the characteristics is shown in FIG. 3. The lifetime evaluation was performed using Polaronix obtained from McScience.

TABLE 1

| | Material for electron transport layer (200 Å) | Operating voltage (at 100 mA/cm$^2$) | Lifetime (half-life of brightness at 100 mA/cm$^2$) |
|---|---|---|---|
| Example 2 | Compound 1 | 7.5 | 600 hours |
| Comparative Example 1 | Alq3 | 9.5 | 440 hours |
| Comparative Example 2 | Znq2 | 8.6 | 380 hours |

Upon comparing operating voltages and lifetimes, it can be seen that the organic light emitting device prepared in Example 2 has more excellent electron transport capability than those prepared in Comparative Examples 1 and 2.

The organometallic complex according to the present invention having excellent electron transport capability and high stability can be effectively used as a material that is used to form an organic layer, and thus an organic light emitting device having low operating voltage and long lifetime can be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex represented by Formula 1:

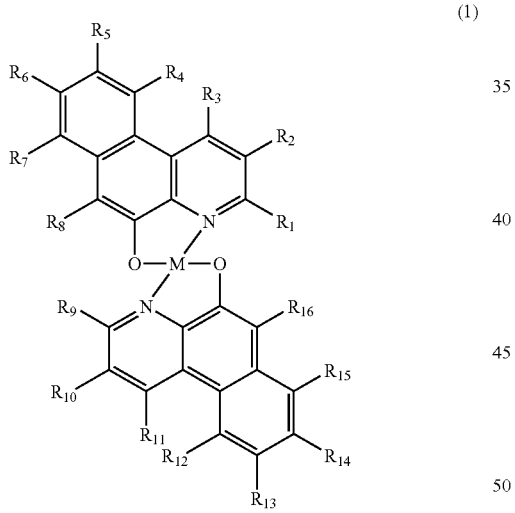

(1)

where $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group; and M is a bivalent metal selected from the group consisting of Be, Mg, Zn, Ca, Cr, Fe, Co, Ni and Cu.

2. The organometallic complex of claim 1, represented by one selected from the group consisting of Formulae 2 through 7:

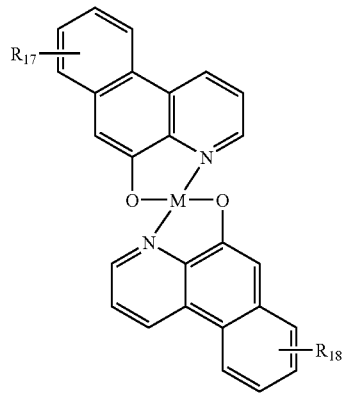

(2)

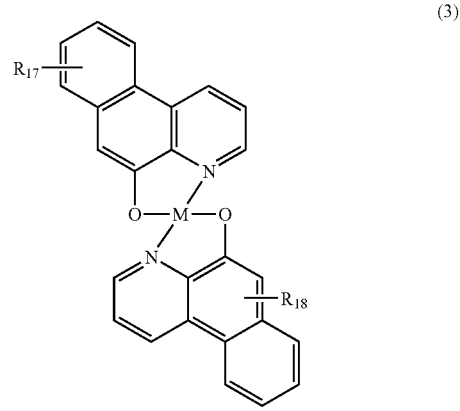

(3)

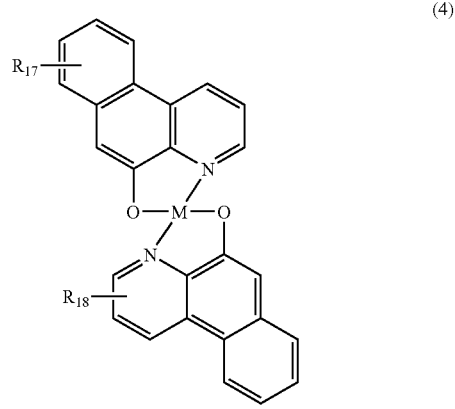

(4)

-continued (5)
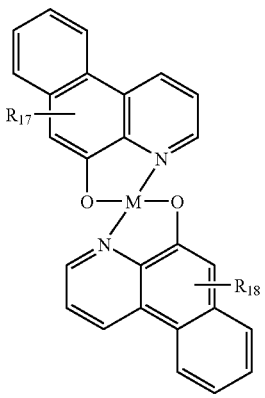

(6)
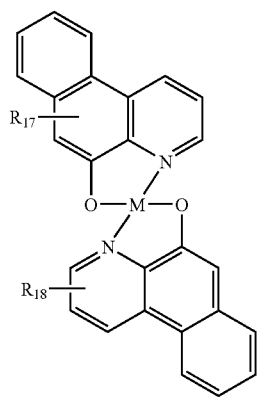

(7)
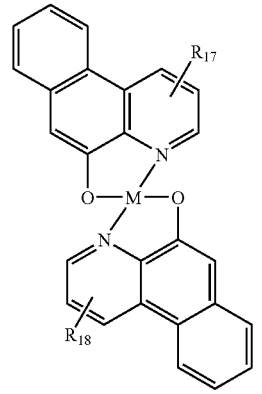

where M is a bivalent metal selected from the group consisting of Be, Mg, Zn, Ca, Cr, Fe, Co, Ni and Cu; and $R_{17}$ and $R_{18}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group.

3. The organometallic complex of claim 1, represented by Formula 8:

(8)
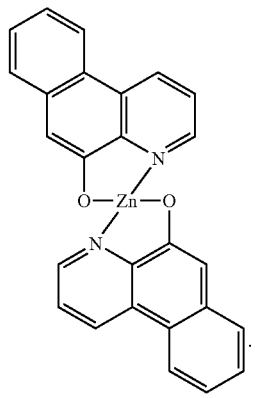

4. The organometallic complex of claim 1, represented by Formula 9:

(9)
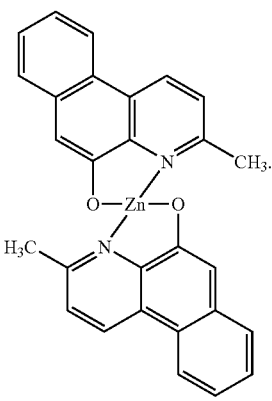

5. The organometallic complex of claim 1, represented by Formula 10:

(10)
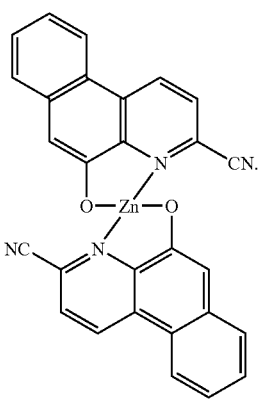

6. An organic light emitting device comprising at least one organic layer comprised of the organometallic complex of claim 1.

7. A method of preparing an organometallic complex represented by Formula 1, the method comprising:

reacting benzoquinolinol derivatives (A) and (A') and a bivalent metal complex (B):

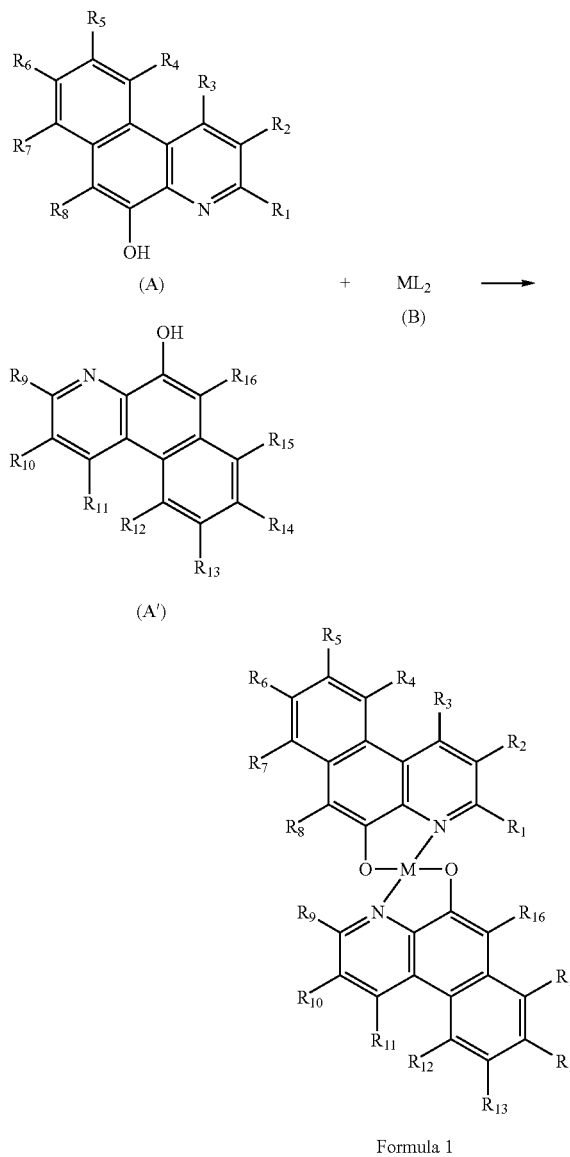

Formula 1 where $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group;

M is a bivalent metal selected from the group consisting of Be, Mg, Zn, Ca, Cr, Fe, Co, Ni and Cu, and L is a monovalent anion ligand.

8. The method of claim 7, wherein the compound (A) is prepared by reacting a naphthalene derivative (C) and a glycerol derivative (D) in the presence of an acid as shown below:

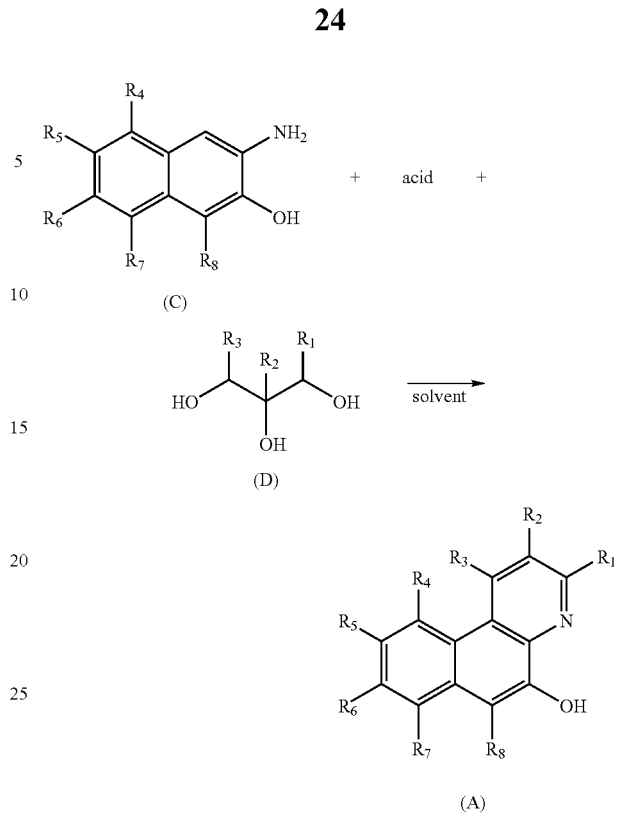

where $R_1$ through $R_8$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group.

9. The method of claim 7, wherein the compound (A') is prepared by reacting a naphthalene derivative (C') and a glycerol derivative (D') in the presence of an acid as shown below:

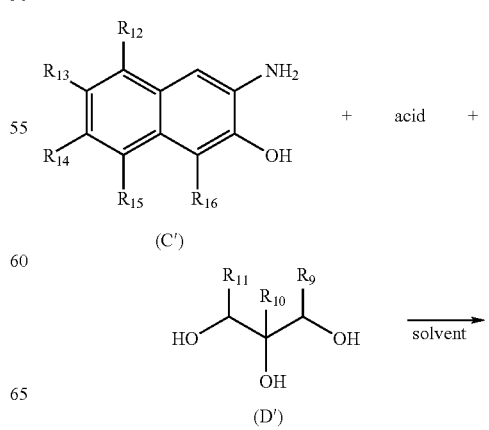

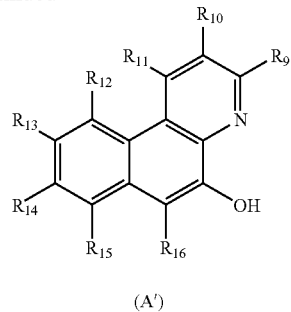

(A')

where $R_9$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group.

10. The method of claim 7, wherein L of the bivalent metal complex (B) is R'COO⁻ where R' is a $C_1$-$C_5$ alkyl group.

11. The method of claim 7, wherein the reaction is performed in a $C_1$-$C_{20}$ alcohol solvent.

12. An organometallic complex prepared from the method of claim 7.

13. An organic light emitting device, comprising:
a first electrode;
a second electrode; and
at least one organic layer between the first electrode and the second electrode, the at least one organic layer comprising an organic layer comprised of an organometallic complex represented by Formula 1:

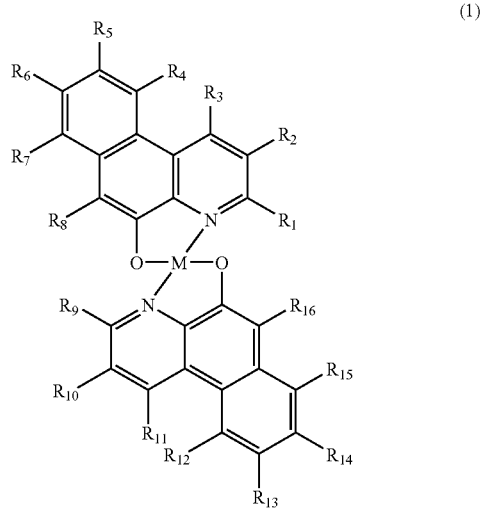

(1)

where $R_1$ through $R_{16}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group; and M is a bivalent metal selected from the group consisting of Be, Mg, Zn, Ca, Cr, Fe, Co, Ni and Cu.

14. The organic light emitting device of claim 13, wherein the organic layer comprised of the organometallic complex is an electron transport layer or an electron injection layer.

15. The organic light emitting device of claim 13, wherein the organic layer comprised of the organometallic complex is an emitting layer.

16. The organic light emitting device of claim 13, wherein said at least one organic layer comprises at least one layer selected from the group consisting of a hole injection layer, a hole transport layer, an emitting layer, a hole blocking layer, an electron transport layer and an electron injection layer.

17. The organic light emitting device of claim 16, wherein said at least one organic layer comprises a hole injection layer, a hole transport layer, an emitting layer, optionally a hole blocking layer, an electron transport layer and an electron injection layer which are sequentially formed on the first electrode.

18. The organic light emitting device of claim 13, wherein the organometallic complex is represented by one selected from the group consisting of Formulae 2 through 7:

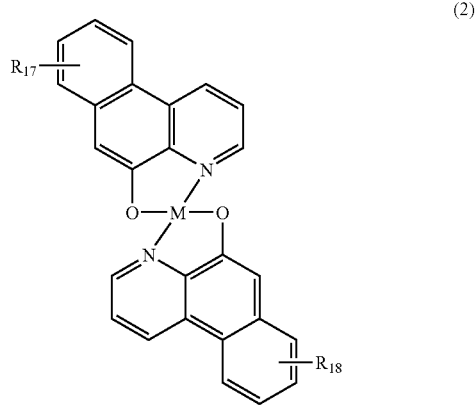

(2)

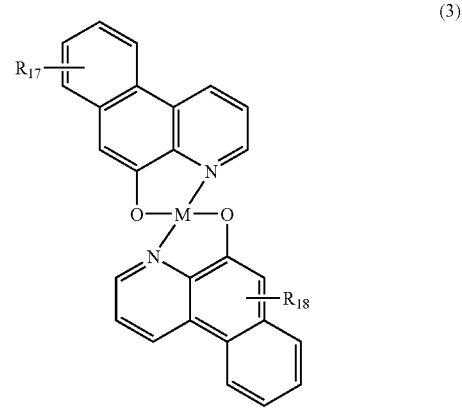

(3)

(4)

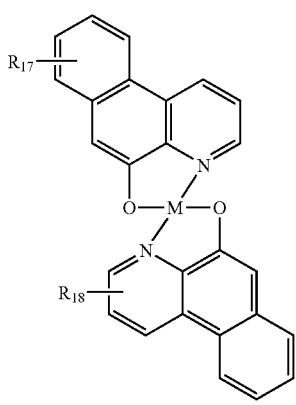

(5)

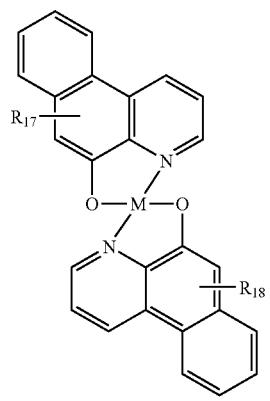

(6)

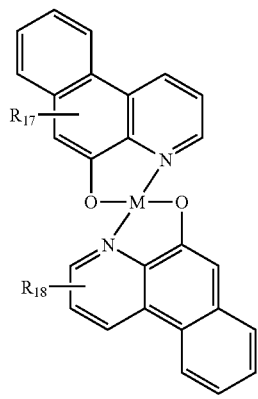

(7)

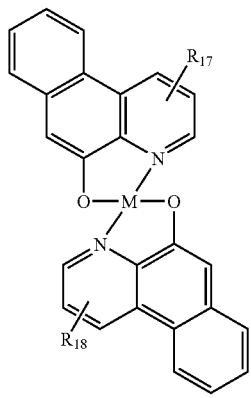

where M is a bivalent metal selected from the group consisting of Be, Mg, Zn, Ca, Cr, Fe, Co, Ni and Cu; and $R_{17}$ and $R_{18}$ are each independently selected from the group consisting of a hydrogen atom, a cyano group, a hydroxyl group, a nitro group, a halogen atom, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_7$-$C_{20}$ arylalkyl group, a substituted or unsubstituted $C_2$-$C_{20}$ alkylalkoxy group, a substituted or unsubstituted $C_7$-$C_{20}$ arylalkoxy group, a substituted or unsubstituted $C_6$-$C_{20}$ arylamino group, a substituted or unsubstituted $C_1$-$C_{20}$ alkylamino group, a substituted or unsubstituted $C_6$-$C_{20}$ heteroarylamino group, and a substituted or unsubstituted $C_2$-$C_{20}$ hetero-ring group.

19. The organic light emitting device of claim 13, wherein the organometallic complex is represented by one selected from the group consisting of Formulae 8 through 10:

(8)

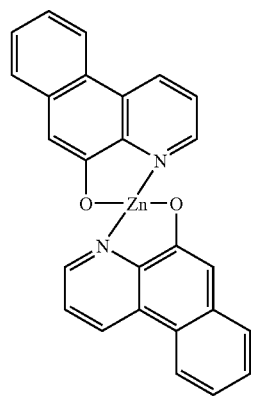

(9)

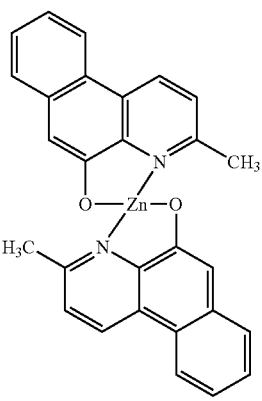

(10)

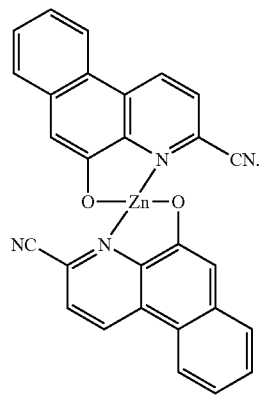

* * * * *